(12) United States Patent
Kim et al.

(10) Patent No.: US 11,028,038 B2
(45) Date of Patent: Jun. 8, 2021

(54) PREPARATION METHOD OF ACRYLIC ESTER COMPOUND

(71) Applicant: LG Chem, Ltd., Seoul (KR)

(72) Inventors: Ji Eun Kim, Daejeon (KR); Won Taeck Lim, Daejeon (KR); Yongjin Kim, Daejeon (KR); Wonmun Choi, Daejeon (KR)

(73) Assignee: LG Chem, Ltd.

( * ) Notice: Subject to any disclaimer, the term of this patent is extended or adjusted under 35 U.S.C. 154(b) by 0 days.

(21) Appl. No.: 16/626,072

(22) PCT Filed: May 15, 2019

(86) PCT No.: PCT/KR2019/006010
§ 371 (c)(1),
(2) Date: Dec. 24, 2019

(87) PCT Pub. No.: WO2020/111410
PCT Pub. Date: Jun. 4, 2020

(65) Prior Publication Data
US 2020/0407308 A1 Dec. 31, 2020

(30) Foreign Application Priority Data

Nov. 27, 2018 (KR) ......................... 10-2018-0148840

(51) Int. Cl.
*C07C 67/08* (2006.01)
*B01J 31/02* (2006.01)
*C07C 69/602* (2006.01)
*C07C 67/02* (2006.01)

(52) U.S. Cl.
CPC ........... *C07C 67/08* (2013.01); *B01J 31/0238* (2013.01); *C07C 67/02* (2013.01); *C07C 69/602* (2013.01)

(58) Field of Classification Search
CPC ....... C07C 67/02; C07C 67/08; C07C 69/602; B01J 31/0238
See application file for complete search history.

(56) References Cited

U.S. PATENT DOCUMENTS

| 4,859,796 | A | * | 8/1989 | Hurtel | ................... | C07D 233/36 |
| | | | | | | 564/204 |
| 6,838,515 | B2 | * | 1/2005 | Derks | ..................... | C07C 67/60 |
| | | | | | | 525/48 |
| 7,321,051 | B2 | | 1/2008 | Yurugi et al. | | |
| 7,368,594 | B2 | | 5/2008 | Yurugi et al. | | |
| 9,051,398 | B2 | | 6/2015 | Tanabe et al. | | |
| 2002/0143120 | A1 | | 10/2002 | Yurugi et al. | | |
| 2011/0137072 | A1 | | 6/2011 | Ansai et al. | | |
| 2011/0301379 | A1 | | 12/2011 | Ansai et al. | | |
| 2014/0005435 | A1 | | 1/2014 | Ansai et al. | | |
| 2015/0038658 | A1 | | 2/2015 | Tanabe et al. | | |
| 2018/0118658 | A1 | | 5/2018 | Hashimoto | | |

FOREIGN PATENT DOCUMENTS

| JP | 2016023153 | A | | 2/2016 | |
| JP | 2017-039918 | | * | 2/2017 | ............ C08F 220/02 |
| JP | 2017039918 | A | | 2/2017 | |
| JP | 6132831 | B2 | | 5/2017 | |
| JP | 2017145220 | A | | 8/2017 | |
| KR | 100543821 | B1 | | 1/2006 | |
| KR | 20110041562 | A | | 4/2011 | |
| KR | 20110112870 | A | | 10/2011 | |
| KR | 20160037002 | A | | 4/2016 | |
| KR | 20160103163 | A | | 8/2016 | |
| KR | 20170136552 | A | | 12/2017 | |
| KR | 20180075313 | A | | 7/2018 | |

OTHER PUBLICATIONS

JP 2017-039918 A, Sumitomo Chemical col. LTD, Resin, Resist Composition and method for producing resist pattern, English Translaiton 99 pages (Year: 2017).*
International Search Report for Application No. PCT/KR2019/006010 dated Sep. 5, 2019, 2 pages.
P. Gentili et al: "2-(Hydroxyimino)aldehydes: Photo- and Physicochemical Properties of a Versatile Functional Group for Monomer Design", Chemistry—A European Journal, vol. 24. May 28, 2018 (May 28, 2018), pp. 7683-7694. XP002801213.
Extended European Search Report for EP19842355.0 dated Dec. 7, 2020; 6 pages.

* cited by examiner

*Primary Examiner* — Yate' K Cutliff
(74) *Attorney, Agent, or Firm* — Lerner, David, Littenberg, Krumholz & Mentlik, LLP

(57) ABSTRACT

The present disclosure relates to a preparation method of an acrylic ester compound. The preparation method of an acrylic ester compound according to the present disclosure enables the use of acrylic anhydride as a reactant instead of acryloyl chloride, which is difficult to handle, by using an alkane diamine as a catalyst. Therefore, not only can the reaction be carried out at a low temperature, but also conversion to an acrylic ester compound and a yield of the acrylic ester compound can be improved.

17 Claims, No Drawings

PREPARATION METHOD OF ACRYLIC ESTER COMPOUND

CROSS-REFERENCE TO RELATED APPLICATIONS

The present application is a national phase entry under 35 U.S.C. § 371 of International Application No. PCT/KR2019/006010 filed May 15, 2019, which claims priority from Korean Patent Application No. 10-2018-0148840 filed Nov. 27, 2018, all of which are incorporated herein by reference.

BACKGROUND OF THE INVENTION

(a) Field of the Invention

The present disclosure relates to a preparation method of an acrylic ester compound, and more particularly, to a technique capable of reacting even at a low temperature and increasing a conversion and a yield of an acrylic ester compound by using an alkane diamine as a catalyst.

(b) Description of the Related Art

Recently, acrylic ester compounds have been used as an internal cross-linking agent for superabsorbent polymers, and their use has been greatly increased. The superabsorbent polymer (SAP) is a type of synthetic polymeric material capable of absorbing 500 to 1000 times its own weight of moisture. Various manufacturers have given it different names, such as SAM (Super Absorbency Material), AGM (Absorbent Gel Material), and the like. Such superabsorbent polymers started to be practically applied in sanitary products, and they are now being widely used not only for hygiene products such as disposable diapers for children, sanitary pads, etc., but also for water retaining soil products for gardening, water stop materials for civil engineering and construction, sheets for raising seedlings, fresh-keeping agents for food distribution fields, materials for poultices, or the like.

In most cases, the superabsorbent polymer is widely used in the field of hygiene products such as diapers and sanitary napkins, and for this purpose, it is necessary to exhibit a high absorption capacity for moisture and the like. In addition, it is necessary that the absorbed moisture should not leak out even under external pressure. Further, it needs to show excellent permeability by maintaining its shape even in an expanded (swelled) state after absorbing water.

Therefore, in order for the superabsorbent polymer to have excellent performance, the base resin, which is the most important constituent polymer, should have high absorption ability.

In order to prepare the base resin, generally, internal cross-linking density of the polymer can be controlled by polymerizing an acrylic acid-based monomer in the presence of an internal cross-linking agent. The internal cross-linking agent is used for cross-linking the interior of a polymer in which an acrylic acid-based monomer is polymerized, that is, a base resin, and the internal cross-linking density of the base resin can be controlled according to the type and content of the internal cross-linking agent. When the cross-linking density of the base resin is low, the absorption ability is increased but strength is weak, so that the shape cannot be maintained in subsequent steps. When the cross-link density is too high, strength is increased but the water absorption ability may be deteriorated. Therefore, it is very important to appropriately control the cross-linking density in view of the strength and the absorption ability of the base resin.

Meanwhile, there has been a problem in the synthesis of the acrylic ester compound which is used as an internal cross-linking agent. When acryloyl chloride is used as a reactant in the preparation of an internal cross-linking agent, it is difficult for workers to handle. On the other hand, when acrylic anhydride is used as a reactant, a reaction temperature is as high as 110° C. or higher, so that a polymerization reaction is likely to proceed between the resulting acrylic esters.

Further, tertiary alcohols used have low reactivity, and triethylamine and 4-dimethylaminopyridine (DMAP) are used as a base in the reaction with acryloyl chloride or acrylic anhydride. In this case, there is a disadvantage in that conversion to an acrylic ester and a yield of the acrylic ester are low.

Therefore, the present inventors found that the addition of an alkane diamine as a catalyst in the synthesis of an acrylic ester as an internal cross-linking agent lowers the reaction temperature, thereby preventing the polymerization reaction between the acrylic esters and increasing the conversion to acrylic ester and the yield of acrylic ester, and they completed the present invention.

PRIOR ART DOCUMENTS

Patent Documents (Patent Document 1) Japanese Patent Publication No. 2017-39918

SUMMARY OF THE INVENTION

The present disclosure describes providing a preparation method of an acrylic ester compound capable of synthesizing the acrylic ester even at a low temperature and increasing conversion to an acrylic ester and a yield of the acrylic ester by using an alkane diamine as a catalyst.

In order to solve the above problems, a preparation method of an acrylic ester compound represented by the following Chemical Formula 4 is provided, including a step of reacting a compound represented by the following Chemical Formula 1 with a compound represented by the following Chemical Formula 2 in the presence of a catalyst represented by the following Chemical Formula 3:

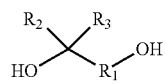

[Chemical Formula 1]

wherein, in Chemical Formula 1,
$R_1$ is a substituted or unsubstituted $C_{1-30}$ alkylene, a substituted or unsubstituted $C_{2-30}$ alkenylene, or a substituted or unsubstituted $C_{2-30}$ alkynylene, and $R_2$ and $R_3$ are each independently hydrogen or a $C_{1-20}$ alkyl,

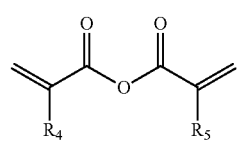

[Chemical Formula 2]

wherein, in Chemical Formula 2, $R_4$ and $R_5$ are each independently hydrogen or a methyl,

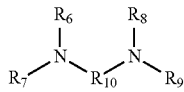

[Chemical Formula 3]

wherein, in Chemical Formula 3, $R_6$ to $R_9$ are each independently hydrogen or a substituted or unsubstituted $C_{1-10}$ alkyl, and $R_{10}$ is a substituted or unsubstituted $C_{1-10}$ alkylene,

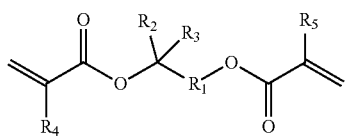

[Chemical Formula 4]

wherein, in Chemical Formula 4, $R_1$ to $R_5$ are as defined above.

The reaction may be carried out at a temperature of 30° C. to 80° C.

A conversion of the reaction may be 90 to 99.9% and a yield of the reaction may be 70 to 95%.

Hereinafter, the present invention will be described in more detail.

As used herein, the term "substituted or unsubstituted" means that it is substituted or unsubstituted with one or more substituent groups selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group containing at least one of N, O, and S atoms, or a substituent group where two or more substituent groups of the exemplified substituent groups are connected. For example, the term "substituent group where two or more substituent groups are connected" may be a biphenyl group. That is, the biphenyl group may be an aryl group, or may be interpreted as a substituent group where two phenyl groups are connected.

In the present disclosure, an alkyl group may be a linear chain or a branched chain, and the number of carbon atoms thereof is not particularly limited but is preferably 1 to 20. According to one embodiment, the alkyl group has 1 to 10 carbon atoms. According to another embodiment, the alkyl group has 1 to 5 carbon atoms. Specific examples of the alkyl group include methyl, ethyl, propyl, n-propyl, isopropyl, butyl, n-butyl, isobutyl, tert-butyl, sec-butyl, 1-methylbutyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present disclosure, the alkenyl group may be a linear chain or a branched chain, and the number of carbon atoms thereof is not particularly limited but is preferably 2 to 30. According to one embodiment, the alkenyl group has 2 to 20 carbon atoms. According to another embodiment, the alkenyl group has 2 to 10 carbon atoms. According to another embodiment, the alkenyl group has 2 to 5 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, the alkynyl group may be a linear chain or a branched chain, and the number of carbon atoms thereof is not particularly limited but is preferably 2 to 30. According to one embodiment, the alkynyl group has 2 to 20 carbon atoms. According to another embodiment, the alkynyl group has 2 to 10 carbon atoms. According to another embodiment, the alkynyl group has 2 to 5 carbon atoms. Specific examples thereof include ethynyl, propynyl, 1-butynyl, 2-butynyl, 1-pentynyl, 2-pentynyl, 3-pentynyl, and the like, but are not limited thereto.

In this disclosure, the description of the alkyl group described above can be applied to the alkylene, except that the alkylene is a divalent group. The description of the alkenyl group described above can be applied to the alkenylene, except that the alkenylene is a divalent group. The description of the alkynyl group described above can be applied to the alkynylene, except that the alkynylene is a divalent group.

The Catalyst

The catalyst according to an embodiment of the present disclosure is represented by the above Chemical Formula 3.

The catalyst represented by Chemical Formula 3 reacts with a reactant to form an acryl-diaminoalkane cation and sequentially form an acrylic ester. Therefore, it is possible to carry out the reaction at a lower temperature than the conventional reaction conditions, thereby reducing possibilities of polymerization between the acrylic ester compounds during the reaction.

When the catalyst of Chemical Formula 3 is used, activation energy of the reaction is lowered by forming the acryl-diaminoalkane cation, which leads to an excellent yield and conversion in the preparation of an acrylic ester. Therefore, this method needs a smaller amount of reactants than the method using the existing catalyst to obtain the same amount of products. Further, since the present method does not require a dropping process, it is simpler than the existing one, so that process time and process costs may be reduced.

Preferably, the $R_6$ to $R_9$ may each independently be hydrogen or a substituted or unsubstituted $C_{1-10}$ alkyl. More preferably, the $R_6$ and $R_7$ may be methyl, and $R_8$ and $R_9$ may be hydrogen or a methyl.

Preferably, the $R_{10}$ may be a substituted or unsubstituted $C_{1-5}$ alkylene. More preferably, the $R_{10}$ may be ethylene.

Most preferably, Chemical Formula 3 may be N,N,N',N'-tetramethylethylenediamine or N,N-dimethylethane-1,2-diamine.

The Acrylic Ester Compound

The acrylic ester compound according to an embodiment of the present disclosure is represented by the above Chemical Formula 4.

The acrylic ester compound represented by Chemical Formula 4 is a pyrolytic internal cross-linking agent, and an internal cross-linking structure of the polymer in which the compound of Chemical Formula 4 and the acrylic acid-based monomer are cross-linked may be decomposed by heat (for example, at 150° C. or higher). Accordingly, when the acrylic acid-based monomer is cross-linked and polymerized in the presence of the acrylic ester compound of Chemical Formula 4, a cross-linked polymer having a pyrolytic internal cross-linked structure may be provided.

In the present disclosure, the "polymer" or "cross-linked polymer" means that the acrylic acid-based monomer is polymerized in the presence of an internal cross-linking agent containing the acrylic ester compound of Chemical Formula 4.

Preferably, the $R_1$ may be a substituted or unsubstituted alkylene, a substituted or unsubstituted $C_{2-10}$ alkenylene, or a substituted or unsubstituted $C_{2-10}$ alkynylene. More preferably, the $R_1$ may be any one selected from the group consisting of 2-methyl-1-pentenylene, 3,3-dimethyl-1-propynylene, propylene, and methyl ethylene.

Preferably, the $R_2$ and $R_3$ may each independently be a $C_{1-5}$ alkyl. More preferably, the $R_2$ and $R_3$ may be a methyl.

Preferably, the $R_4$ and $R_5$ may be hydrogen.

The Preparation Method of an Acrylic Ester Compound

The preparation method of an acrylic ester compound according to an embodiment of the present disclosure includes a step of reacting the compound of Chemical Formula 1 and the compound of Chemical Formula 2 as reactants in the presence of the catalyst of Chemical Formula 3.

In the above preparation method, $R_1$ to $R_5$ of Chemical Formulae 1 and 2, which are reactants, are the same as described in the above acrylic ester compound.

In the above preparation method, $R_6$ to $R_{10}$ of Chemical Formula 3, which is a catalyst, are the same as described in the above catalyst.

More preferably, Chemical Formula 1 may be any one of the following Chemical Formulae 1-1 to 1-4.

[Chemical Formula 1-1]

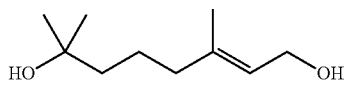

[Chemical Formula 1-2]

[Chemical Formula 1-3]

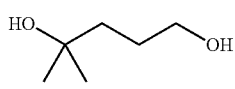

[Chemical Formula 1-4]

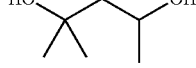

More preferably, Chemical Formula 2 may be acrylic anhydride.

In the preparation of the acrylic ester compound, 2.1 to 3.5 equivalents of the compound represented by Chemical Formula 2 and 0.05 to 0.5 equivalents of the catalyst represented by Chemical Formula 3 are reacted based on 1 equivalent of the compound represented by Chemical Formula 1.

The step of reacting the compound represented by Chemical Formula 1 with the compound represented by Chemical Formula 2 may be carried out for 4 hours or more, 6 hours or more, 8 hours or more, 10 hours or more, or 12 hours or more; and for 24 hours or less.

The step of reacting the compound represented by Chemical Formula 1 with the compound represented by Chemical Formula 2 may be carried out at a temperature of 30° C. to 80° C., 35° C. to 75° C., or 40° C. to 70° C. When the reaction temperature is lower than 30° C., the conversion may be lowered. When the reaction temperature is higher than 80° C., there is a disadvantage in that a polymerization reaction is likely to proceed between the acrylic esters, thereby lowering the yield.

The conversion to the compound represented by Chemical Formula 4 may be 90 to 99.9%, 93 to 99.9%, 95 to 99.9%, or 95 to 99%. The yield of the compound represented by Chemical Formula 4 may be 70 to 95%, 75 to 95%, 75 to 90%, 75 to 87%, or 78 to 87%. The compound represented by Chemical Formula 4 obtained by the above preparation method may be used as a cross-linking agent in the polymerization of an acrylic acid-based monomer, but is not limited thereto.

The preparation method of an acrylic ester compound according to the present disclosure enables the use of acrylic anhydride as a reactant instead of acryloyl chloride, which is difficult to handle, by using an alkane diamine as a catalyst, and enables the reaction to be carried out at a low temperature. At the same time, this preparation method can improve conversion to an acrylic ester compound and a yield of the acrylic ester compound.

DETAILED DESCRIPTION OF THE EMBODIMENTS

Hereinafter, the present invention will be explained in detail with reference to the following examples. However, these examples are only to illustrate the invention, and the scope of the invention is not limited thereto.

Example 1

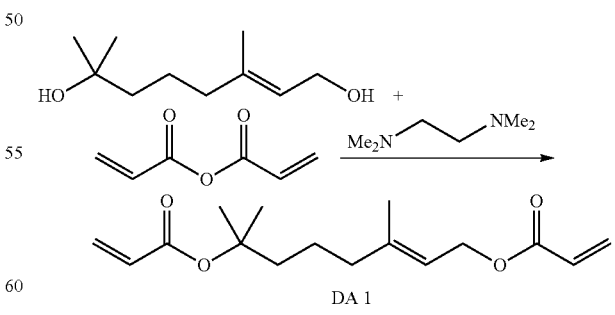

3,7-dimethyl-2-octene-1,7-diol (30.0 g, 174 mmol), N,N,N',N'-tetramethylethylenediamine (6.07 g, 52.2 mmol, 0.30 eq.), and acrylic anhydride (65.89 g, 522.4 mmol, 3.0 eq.) were placed in a 250 mL round-bottom flask, and reacted at 60° C. for 12 hours or more. Thereafter, it was filtered using a celite pad with 300 mL of n-hexane, and concentrated to obtain a product DA 1 (39.1 g, yield 80%).

¹H NMR (500 MHz, CDCl₃): δ 6.39-6.02 (m, 2H), 6.01-5.80 (m, 2H), 5.75-5.72 (m, 2H), 5.44-5.37 (m, 2H), 4.69-4.65 (m, 2H), 2.15-2.03 (m, 2H), 1.77-1.23 (m, 13H).

Example 2

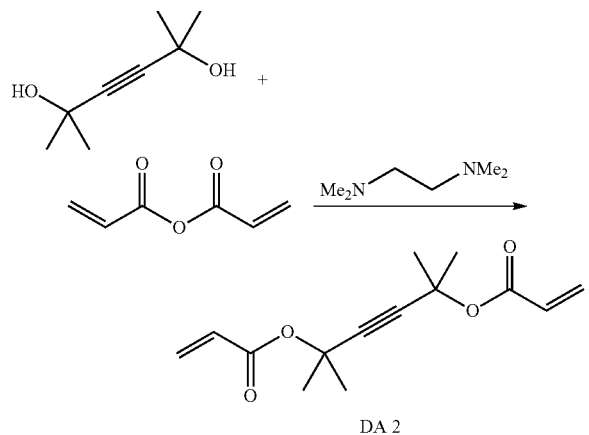

DA 2

2,5-dimethyl-3-hexyne-2,5-diol (30.0 g, 210.9 mmol), N,N,N',N'-tetramethylethylenediamine (7.36 g, 63.3 mmol, 0.30 eq.), and acrylic anhydride (79.82 g, 632.9 mmol, 3.0 eq.) were placed in a 250 mL round-bottom flask, and reacted at 60° C. for 12 hours or more. Thereafter, it was filtered using a celite pad with 300 mL of n-hexane, and concentrated to obtain a product DA 2 (43.8 g, yield 83%).

¹H NMR (500 MHz, CDCl₃): δ 6.34 (dd, 2H), 6.06 (dd, 2H), 5.76 (dd, 2H), 1.68 (s, 12H).

Example 3

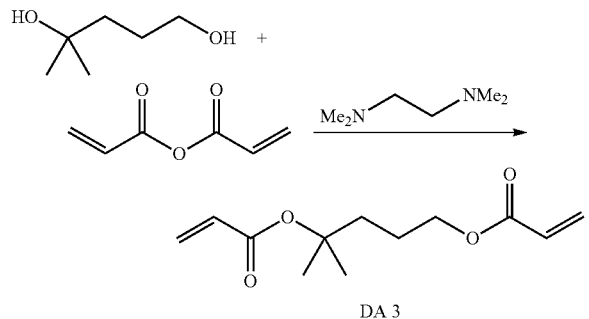

DA 3

4-methylpentane-1,4-diol (20.0 g, 169 mmol), N,N,N',N'-tetramethylethylenediamine (5.9 g, 50.8 mmol, 0.30 eq.), and acrylic anhydride (64.03 g, 508 mmol, 3.0 eq.) were placed in a 250 mL round-bottom flask, and reacted at 60° C. for 12 hours or more. Thereafter, it was filtered using a celite pad with 200 mL of n-hexane, and concentrated to obtain a product DA 3 (32.9 g, yield 86%).

¹H NMR (500 MHz, CDCl₃): δ 6.43 (1H, dd), 6.32 (2H, dd), 6.13 (1H, dd), 6.04 (1H, dd), 5.84 (1H, dd), 5.77 (1H, dd), 4.17 (2H, t), 1.88 (2H, m), 1.75 (2H, m), 1.50 (6H, s).

Example 4

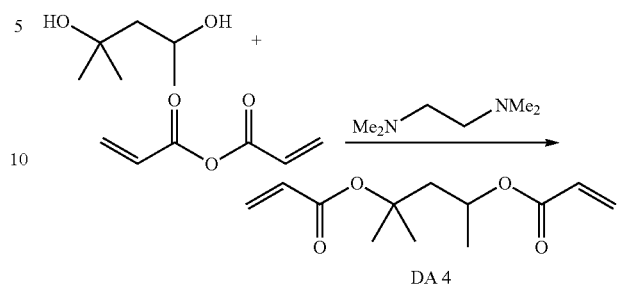

DA 4

2-methylpentane-2,4-diol (20.0 g, 169 mmol), N,N,N',N'-tetramethylethylenediamine (5.9 g, 50.8 mmol, 0.30 eq.), and acrylic anhydride (64.03 g, 508 mmol, 3.0 eq.) were placed in a 250 mL round-bottom flask, and reacted at 60° C. for 12 hours or more. Thereafter, it was filtered using a celite pad with 200 mL of n-hexane, and concentrated to obtain a product DA 4 (31.8 g, yield 83%).

¹H NMR (500 MHz, CDCl₃): δ 6.38 (1H, dd), 6.31 (1H, dd), 6.08 (1H, dd), 6.01 (1H, dd), 5.25 (1H, m), 1.57 (3H, s), 1.51 (6H, s), 1.28 (2H, d).

Example 5

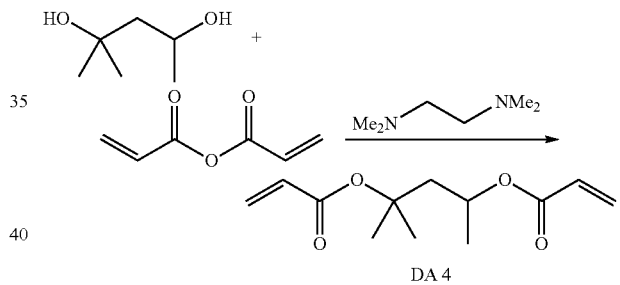

DA 4

2-methylpentane-2,4-diol (20.0 g, 169 mmol), N,N-dimethylethane-1,2-diamine (4.5 g, 50.8 mmol, 0.30 eq.), and acrylic anhydride (64.03 g, 508 mmol, 3.0 eq.) were placed in a 250 mL round-bottom flask, and reacted at 60° C. for 12 hours or more. Thereafter, it was filtered using a celite pad with 200 mL of n-hexane, and concentrated to obtain a product DA 4 (31.8 g, yield 79%).

¹H NMR (500 MHz, CDCl₃): δ 6.38 (1H, dd), 6.31 (1H, dd), 6.08 (1H, dd), 6.01 (1H, dd), 5.25 (1H, m), 1.57 (3H, s), 1.51 (6H, s), 1.28 (2H, d).

Comparative Example 1

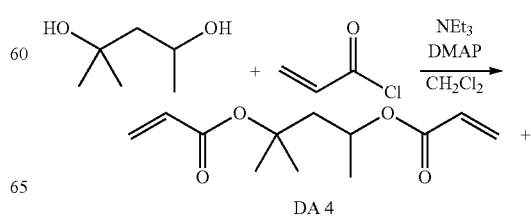

DA 4

-continued

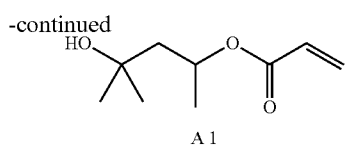

A 1

2-methylpentane-2,4-diol (20.0 g, 169 mmol), methylene chloride (120 mL), triethylamine (51.38 g, 508 mmol, 3.0 eq.), and and 4-dimethylaminopyridine (2.07 g, 16.92 mmol, 0.1 eq.) were placed in a 250 mL round-bottom flask, and a solution of acryloyl chloride (45.95 g, 507.7 mmol, 3.0 eq.) and methylene chloride (50 mL) was slowly added thereto at 0° C. for 2 hours. Thereafter, they reacted at 0° C. for 1 hour, and the temperature was gradually raised to room temperature, followed by reacting for 12 hours. Then, methylene chloride, which is a solvent, was removed under reduced pressure, diluted with 200 mL of n-hexane and washed twice with 200 mL of water. Magnesium sulfate was added to the n-hexane solution to remove water, and the mixture was filtered using a celite pad and then concentrated to obtain a mixture of DA 4 and A 1.

Comparative Example 2

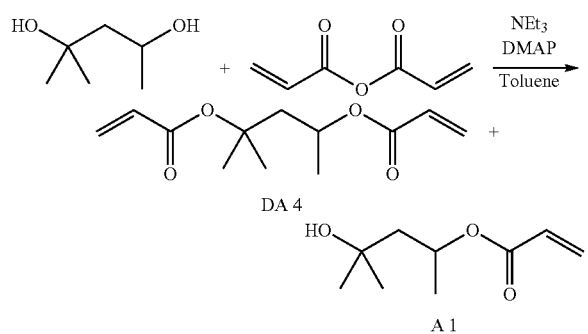

2-methylpentane-2,4-diol (20.0 g, 169 mmol), toluene (170 mL), triethylamine (51.38 g, 508 mmol, 3.0 eq.), and 4-dimethylaminopyridine (2.07 g, 16.92 mmol, 0.1 eq.) were placed in a 250 mL round-bottom flask, and acrylic anhydride (64.03 g, 507.7 mmol, 3.0 eq.) was slowly added thereto at 110° C. for 2 hours. Thereafter, they reacted at 110° C. for 12 hours. Then, toluene, which is a solvent, was removed under reduced pressure, diluted with 200 mL of n-hexane, and washed twice with 200 mL of water. Magnesium sulfate was added to the n-hexane solution to remove water, and the mixture was filtered using a celite pad and then concentrated to obtain a mixture of DA 4 and A 1.

Experimental Example

The conversion and yield were calculated according to the following Formulae 1 and 2 for the above examples and comparative examples, respectively, and the results are shown in Table 1 below.

Conversion (%)=[(the number of moles of acrylic ester prepared before extraction)/(the number of moles of Chemical Formula 1 provided)]*100    [Formula 1]

Yield (%)=[(the number of moles of acrylic ester prepared after extraction)/(the number of moles of Chemical Formula 1 provided)]*100    [Formula 2]

TABLE 1

| | Reactant | Catalyst | Conversion to DA (%) | Ratio of DA:A | Yield of DA (%) |
|---|---|---|---|---|---|
| Ex.1 | Acrylic anhydride | N,N,N',N'-tetramethylethyl-enediamine | 98 | 98:2 | 80 |
| Ex.2 | Acrylic anhydride | N,N,N',N'-tetramethylethyl-enediamine | 99 | 99:1 | 83 |
| Ex.3 | Acrylic anhydride | N,N,N',N'-tetramethylethyl-enediamine | 99 | 99:1 | 86 |
| Ex.4 | Acrylic anhydride | N,N,N',N'-tetramethylethyl-enediamine | 98 | 98:2 | 83 |
| Ex.5 | Acrylic anhydride | N,N-dimethylethane-1,2-diamine | 95 | 98:2 | 79 |
| Comp.Ex.1 | Acryloyl chloride | NEt$_3$, DMAP | 85 | 86:14 | 62 |
| Comp.Ex.2 | Acrylic anhydride | NEt$_3$, DMAP | 80 | 80:20 | 52 |

Referring to Table 1, Examples 1 to 5 using N,N,N',N'-tetramethylethylenediamine or N,N-dimethylethane-1,2-diamine as a catalyst had a conversion to acrylic ester of 95% or more and a yield of acrylic ester of 79% or more, which are superior to the comparative examples using NEt$_3$ and DMAP as a catalyst.

Further, it was confirmed that all of Examples 1 to 5 had excellent conversion and yield as shown in Table 1 even though the reaction proceeded at a temperature of 60° C., which is significantly lower than the esterification temperature of acrylic anhydride (110° C.) of Comparative Example 2.

What is claimed is:

1. A preparation method of an acrylic ester compound represented by the following Chemical Formula 4, comprising a step of reacting a compound represented by the following Chemical Formula 1 with a compound represented by the following Chemical Formula 2 in the presence of a catalyst represented by the following Chemical Formula 3:

[Chemical Formula 1]

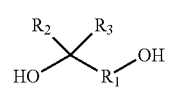

wherein, in Chemical Formula 1,
R$_1$ is a substituted or unsubstituted C$_{1-30}$ alkylene, a substituted or unsubstituted C$_{2-30}$ alkenylene, or a substituted or unsubstituted C$_{2-30}$ alkynylene, and
R$_2$ and R$_3$ are each independently hydrogen or a C$_{1-20}$ alkyl,

[Chemical Formula 2]

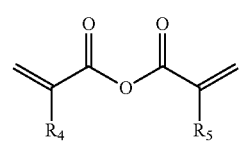

wherein, in Chemical Formula 2,
R$_4$ and R$_5$ are each independently hydrogen or a methyl,

[Chemical Formula 3]

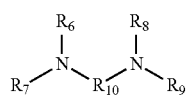

wherein, in Chemical Formula 3,
R₆ to R₉ are each independently hydrogen or a substituted or unsubstituted $C_{1-10}$ alkyl, and
$R_{10}$ is a substituted or unsubstituted $C_{1-10}$ alkylene,

[Chemical Formula 4]

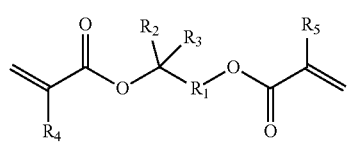

wherein, in Chemical Formula 4,
$R_1$ to $R_5$ are as defined above.

2. The preparation method of claim 1,
wherein the $R_1$ is a substituted or unsubstituted $C_{1-10}$ alkylene, a substituted or unsubstituted $C_{2-10}$ alkenylene, or a substituted or unsubstituted $C_{2-10}$ alkynylene.

3. The preparation method of claim 1,
wherein the $R_2$ and $R_3$ are each independently a $C_{1-5}$ alkyl.

4. The preparation method of claim 3,
wherein the $R_2$ and $R_3$ are methyl.

5. The preparation method of claim 1,
wherein the $R_4$ and $R_5$ are hydrogen.

6. The preparation method of claim 1,
wherein the $R_6$ to $R_9$ are each independently a substituted or unsubstituted $C_{1-10}$ alkyl.

7. The preparation method of claim 1,
wherein the $R_6$ and $R_7$ are methyl, and
$R_8$ and $R_9$ are hydrogen or methyl.

8. The preparation method of claim 1,
wherein the $R_{10}$ is a substituted or unsubstituted $C_{1-5}$ alkylene.

9. The preparation method of claim 8,
wherein the $R_{10}$ is ethylene.

10. The preparation method of claim 1,
wherein Chemical Formula 1 is any one of the following Chemical Formulae 1-1 to 1-4:

[Chemical Formula 1-1]

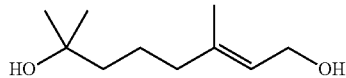

[Chemical Formula 1-2]

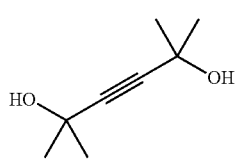

[Chemical Formula 1-3]

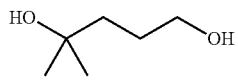

[Chemical Formula 1-4]

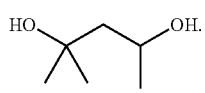

11. The preparation method of claim 1,
wherein the compound represented by Chemical Formula 2 is acrylic anhydride.

12. The preparation method of claim 1,
wherein the catalyst represented by Chemical Formula 3 is N,N,N',N'-tetramethylethylenediamine or N,N-dimethylethane-1,2-diamine.

13. The preparation method of claim 1,
wherein the reaction is carried out at a temperature of 30° C. to 80° C.

14. The preparation method of claim 1,
wherein conversion of the reaction is 90 to 99.9% and a yield of the reaction is 70 to 95% a.

15. The preparation method of claim 1,
wherein the $R_1$ is any one selected from the group consisting of 2-methyl-1-pentenylene, 3,3-dimethyl-1-propynylene, propylene, and methyl ethylene.

16. The preparation method of claim 1, wherein 2.1 to 3.5 equivalents of the compound represented by Chemical Formula 2 and 0.05 to 0.5 equivalents of the compound represented by Chemical Formula 3 are reacted based on 1 equivalent of the compound represented by Chemical Formula 1.

17. The preparation method of claim 1, wherein the step of reacting the compound represented by Chemical Formula 1 with the compound represented by Chemical Formula 2 is carried out from 4 hours to 24 hours.

* * * * *